United States Patent
Sambanthamurthi et al.

(10) Patent No.: US 9,919,020 B2
(45) Date of Patent: Mar. 20, 2018

(54) BIOACTIVE COMPOUND OBTAINED FROM OIL PALM BASE MATERIALS

(71) Applicant: MALAYSIAN PALM OIL BOARD, Kajang, Selangor (MY)

(72) Inventors: Ravigadevi Sambanthamurthi, Kajang (MY); Yew Ai Tan, Kajang (MY); Syed Fairus Abu Bakar, Kajang (MY); Che Anishas Idris, Kajang (MY); Soon Sen Leow, Kajang (MY); Mohd Jamil Elias, Kajang (MY); Wan Saridah Wan Omar, Kajang (MY); Mohd Sofian Mohamad Ideris, Kajang (MY); Jabariah Md. Ali, Kajang (MY)

(73) Assignee: Malaysian Palm Oil Board, Kajang, Selangor (MY)

( * ) Notice: Subject to any disclaimer, the term of this patent is extended or adjusted under 35 U.S.C. 154(b) by 0 days.

(21) Appl. No.: 14/417,741

(22) PCT Filed: Jul. 26, 2013

(86) PCT No.: PCT/MY2013/000135
§ 371 (c)(1),
(2) Date: Jan. 27, 2015

(87) PCT Pub. No.: WO2014/017900
PCT Pub. Date: Jan. 30, 2014

(65) Prior Publication Data
US 2015/0202245 A1    Jul. 23, 2015

(30) Foreign Application Priority Data
Jul. 27, 2012  (MY) .............................. PI2012700505

(51) Int. Cl.
*A61K 36/889*  (2006.01)
*A61K 31/05*  (2006.01)

(52) U.S. Cl.
CPC ............ *A61K 36/889* (2013.01); *A61K 31/05* (2013.01); *A61K 2236/00* (2013.01)

(58) Field of Classification Search
CPC .................................................. A61K 36/889
USPC .................................................. 424/727, 777
See application file for complete search history.

(56) References Cited

U.S. PATENT DOCUMENTS

2003/0031740 A1*  2/2003  Sambanthamurthi et al. ............................ 424/777

OTHER PUBLICATIONS

Sambanthamurthi, R. et al., "Oil palm vegetation liquor: a new source of phenolic bioactives", British Journal of Nutrition, 2011, vol. 106, pp. 1655-1663. See abstract: Figure 1B; and pp. 1655, 1656, and 1662, Webpage: http://web.mit.edu/biology/sinskey/www/Sambanthamurthi_oilpalmliquor2011.pdf.
Gan, P. P. et al., "Green synthesis of gold nanoparticles using palm oil mill effluent (POME): a low-cost and eco-friendly viable approach", Bioresource Technology, Jan. 14, 2012 (E-pub), vol. 113, pp. 132-135, See abstract; and pp. 132 and 135. Webpage: http://www.ncbi.nlm.nih.gov/pubmed/22297042.
Wu, T. Y. et al., "A holistic approach to managing palm oil mill effluent (POME): biotechnological advances in the sustainable reuse of POME", Biotechnology Advances, 2009, vol. 27, pp. 40-52. See abstract, and pp. 1243 and 1247. Webpage: http://www.ncbi.nlm.nih.gov/pubmed/18804158.
Han, N.M. et al., "Determination of antioxidants in oil palm leaves (Elaeis guineensis)", American Journal of Applied Sciences, 2010, vol. 7, No. 9, pp. 1243-1247. Webpage: http://thescipub.com/PDF/ajassp.2010.1243.1247.pdf.
Neo, Y. P. et al., "Determination of oil palm fruit phenolic compounds and their antioxidant activities using spectrophotometric methods", International Journal of Food Science and Technology, 2008, vol. 43, pp. 1832-1837. See abstract, and pp. 1832and 1833. Webpage: http://psasir.upm.edu.my/13956/.

* cited by examiner

*Primary Examiner* — Chris R Tate
*Assistant Examiner* — Deborah Davis
(74) *Attorney, Agent, or Firm* — Merchant & Gould P.C.

(57) ABSTRACT

This disclosure is directed to a novel bioactive compound obtained from oil palm based materials and compositions containing said bioactive compound. The bioactive compound obtained in accordance with the present invention has a molecular mass of 482. The bioactive compound also has potent HIV reverse transcriptase activity and antioxidant activity.

2 Claims, 2 Drawing Sheets

US 9,919,020 B2

BIOACTIVE COMPOUND OBTAINED FROM OIL PALM BASE MATERIALS

CROSS-REFERENCE TO RELATED APPLICATIONS

This application is a National Stage Application of International Application No. PCT/MY2013/000135, filed 26 Jul. 2013, which claims benefit of Malaysian Serial No. PI 2012700505, filed 27 Jul. 2012 in Malaysia and which applications are incorporated herein by reference in their entireties. To the extent appropriate, a claim of priority is made to each of the above disclosed applications.

FIELD OF INVENTION

The invention generally relates to bioactive compounds and more particularly to a phenolic compound obtained from plants and plant-based material, with said compound exhibiting highly significant bioactive properties.

BACKGROUND OF INVENTION

The demand for bioactive compounds is expected to increase dramatically with the increase in world population and thus the need for various industrial and pharmaceutical uses, e.g in the use of manufacturing medical remedies such as anti-viral drugs particularly in the event of a pandemic outbreak.

At present a great majority of bioactive compounds are generally found in substantially low concentrations. In addition, the process or method of extraction is expensive. Further, the scarce availability of bioactive compounds has hampered the potential production of medicaments, and thus stresses the need for other abundant sources. Accordingly, it would be desirable to explore other low cost and abundant sources for bioactive compounds in order to aid in fulfilling the surging global demand.

The present application focuses on realizing the value and potential of the vegetation liquor and oil palm based materials from palm oil milling and palm oil mill effluent (POME) as a source of bioactive compounds.

The present invention discloses oil palm based materials including the vegetation liquor of palm oil milling as an abundant source of bioactive compounds.

SUMMARY OF INVENTION

In one aspect there is provided a composition comprising a bioactive compound obtained from oil palm based materials, wherein the molecular weight of said phenolic compound is 482.

In another aspect there is provided the use of a compound obtained from oil palm based materials as the active ingredient for the preparation of a composition useful for providing bioactive properties, whereby the molecular weight of said compound is 482.

BRIEF DESCRIPTION OF DRAWINGS

Some figures contain color representations or entities in order to elucidate the results of experiments for the purpose of the present invention.

DETAILED DESCRIPTION OF THE PREFERRED EMBODIMENTS

Figure 1:
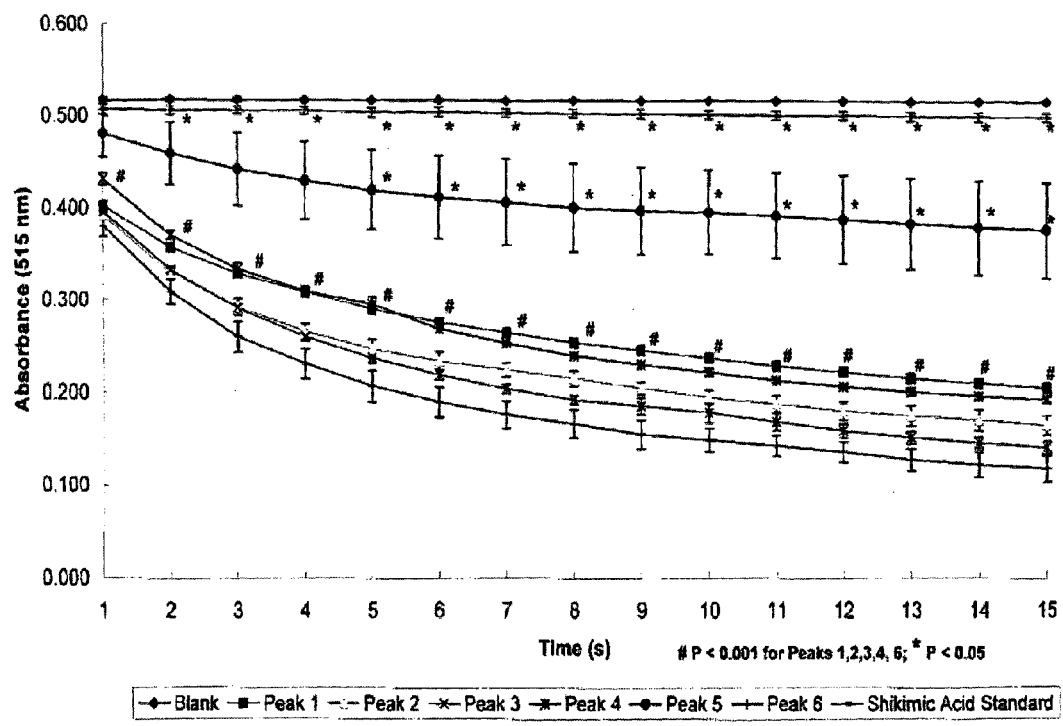
FIG. 1 shows the results obtained based on DPPH Scavenging Assay with respect to the compound in accordance with a preferred embodiment of the claimed invention.

The disclosed description and examples are directed to a bioactive compound, composition and method thereof, whereby the bioactive compound with molecular weight of 482 is extracted from oil palm based materials.

The biologically active extracts of palm vegetation liquor useful in this invention are those obtained from the vegetation liquor of the palm oil milling process according to various conventional suitable means and processes.

Although the extract may contain a variety of compounds including phenolic compounds, fruit acids, fruit sugars and glycerol, starch, cellulose and hemicellulose, for purposes of standardization the concentrations of the extracts used were measured in terms of phenolic content i.e gallic acid equivalent.

Embodiments of the present invention are directed to a composition comprising a bioactive compound and other major phenolic compounds obtained from any part of the oil palm, oil palm based materials including vegetation liquor of palm oil processing and palm oil mill effluent. The composition of the present invention can be prepared based on available or standard methods. It is expected that the preparation is safe and said composition is suitable for use in, but not limiting to, daily consumption including dietary supplements, nutraceuticals, and for health promoting purposes. It is further noted that the bioactive compound and its derivatives obtained based on the preferred embodiments of the present invention are suspected to exhibit antiviral and antimicrobial effects.

It would be apparent to a person skilled in the art that the raw extracts obtained from any part of the oil palm, or oil palm based materials, including the vegetation liquor from palm oil milling and palm oil mill effluent for the purpose of the present invention may contain various other phenolic compounds in addition to the novel primary marker bioactive compound.

The extracts obtained from oil palm based materials and more particularly for this disclosure, the vegetation liquor from palm oil milling and palm oil mill effluent when subjected to isolation and purification stages in accordance with the method of the present invention are found to contain a novel bioactive compound or their derivatives.

The present invention extends, therefore to a novel bioactive compound; and method thereof, whereby the primary steps of said method are pre-treatment of raw extracts obtained from any part of the oil palm, the vegetation liquor from palm oil milling and palm oil mill effluents. This embodiment encompasses isolation of substantially purified bioactive compound having molecular weight of 482. It should be noted that an "isolated or purified" bioactive compound or biologically active portion thereof, is substantially free of other cellular materials or other components or substantially free of chemical precursors or other chemicals.

The following examples serve to merely explain different methods of preparing the bioactive compound and related compounds and should not be construed to confine the scope of claims. In accordance with a preferred embodiment, the extracts obtained from the oil palm based materials, may be subjected to a pretreatment process. Such process may be performed as portrayed in EXAMPLE 1 below.

Example 1

Pretreatment of Extracts

The first step of the method for preparation of the composition containing the bioactive compound is pre-treatment of the raw extracts to obtain pre-concentrated or partially purified extracts. This may be performed with low stringent conditions of subjecting the extracts to a flash chromatography or the likes, or alternatively, subjecting said extracts to ethanol precipitation, prior to separation by high performance liquid chromatography. An example of such method is given by way of reference below and should not be construed as limiting the scope of the claims.

The main steps involved for the first approach is loading a "sep-pak" type column, removing impurities, eluting said extracts with methanol or ethanol and subjecting said extracts for concentration stage in a rotary evaporator. The second approach comprises the steps of adding an amount of extract to three volumes of cold ethanol (EtOH), storing said mixture overnight at a preferred temperature of −20° C., centrifuging at 1500×g for at least 15 minutes, dissolving the precipitate obtained from the previous step with a suitable amount of distilled water and concentrating by rotary evaporator at 50° C. to obtain the preferred final value of 3 ml. It should be mentioned that these steps for both approaches might be substituted with alternative steps of standard procedures known in the art to achieve a similar objective.

The next imperative step of the method for the preparation of the composition as disclosed involves the isolation and purification of the phenolic compound from the partially purified or pre-treated extracts. This can be carried out with the conventional high performance liquid chromatography (HPLC) based on low stringent conditions or parameters. An example of such method is given by way of reference below and should not be construed as limiting the scope of the claims.

Example 2

Isolation and Purification of Phenolic Compounds from Oil Palm Based Materials An econosil C18 5 µm particle size, with the preferred column length of 25 cm×10 mm id, flow rate of 3 ml per minute was prepared. The preferred mobile phase gradient may comprise two solvents, with one solvent consisting of 0.1% trifluoroacetic acid (TFA) with an amount of water and another solvent consisting of 10/90 of 0-1% TFA/acetonitrile (ACN) v/v. In this study, the injection column was 1 ml and readings were taken at 280 nm. The mixture is subjected to isolation by HPLC and it is observed that there are several peaks, at least one peak indicating the elution of the compound within 30 to 35 minutes. Further details of the peaks will be described in the next example, which is the peak isolation segment.

It would be understood that the choice of columns and parameters for HPLC may vary however to obtain a similar result of elution time as described. Eluted fraction may be suitably collected and provided in powder or liquid form for use in further analysis.

Example 3

Peak Isolation

The HPLC chromatogram obtained from the injection of concentrated sample was observed. Identification of peak fractions was based on retention time. From the chromatogram, there were several peaks observed, wherein each of the peak fractions was subjected to structural and chemical identification.

Example 4

Molecular Weights of Peaks

The molecular weights of the six major peaks collected were obtained using standard Liquid Chromatography-Mass Spectrometry (LC-MS). From the results, it was observed that peak 6 has a molecular mass of 482.

Example 5

Profiling—Free Radical Scavenging

Fractions 1 to 6 were further analysed for their properties in free radical scavenging. The free radical form of DPPH. is purple in colour and absorbs maximally at a wavelength of 515 nm. Antioxidants such as certain phenolic compounds are able to scavenge the free radicals of DPPH. resulting in a decrease in intensity of the purple colour, which can be measured spectrophotometrically.

Free Radical Scavenging Assay

Stock solution of DPPH. was diluted to 0.025 mg/ml with water to give a final solution in 50% methanol. Gallic acid was prepared at the concentration of 300 ppm (300 µg/ml). Substances to be tested were prepared in water to give a concentration of 300 ppm GAE.

To 975 µl of DPPH. solution in a cuvette, 25 µl of sample was added. Absorbance at the wavelength of 515 nm was monitored spectrophotometrically at 0.1 min intervals for 2 min. The control was treated in the same manner except that the sample was replaced with water. Blank contained 50% of methanol in place of DPPH. and water in place of sample. Values for the blank were subtracted from the test values.

Concentration of DPPH. at any particular absorbance was calculated from the DPPH. standard curve using the formula, $$Y = aX + b$$

Where,
Y=absorbance (at 515 nm)
X=concentration of DPPH. (µg/mL)
a=Linear regression coefficient
b=y-intercept
Since the standard curve passes through the origin, therefore b=0
Rearranging the formula, $$X = \frac{Y}{a} \tag{3}$$

The percentage of DPPH. remaining (% DPPH.$_{rem}$) was calculated using the formula, $$\% \ DPPH^*_{rem} = \frac{[DPPH]_0 - [DPPH^0]_t}{[DPPH^0]_0} \times 100\% \quad (4)$$

Where,
[DPPH.]$_t$=concentration of DPPH. at t time (μg/ml)
[DPPH.]$_0$=initial concentration of DPPH. (μg/ml)

Percentages of DPPH. remaining against time were plotted and the graph obtained is shown in FIG. 1. According to the results obtained, peak 6 exhibited the strongest DPPH free-radical scavenging activity owing to its lowest absorption compound to other peaks.

Further chemical analysis on determining the properties of the phenolic compound based on the peaks as obtained in accordance with the method of the present invention may be carried out based on conventional or standard procedures known in the art.

Example 6

Reverse Transcriptase Assay: Inhibitor Determination

Fractions of 1 to 6 were further analyzed for protease and HIV reverse transcriptase inhibiting properties. In accordance with one embodiment of the present invention, the purified fraction of peak 6 of the disclosed invention has shown potent inhibitory action against both HIV protease and reverse transcriptase. Compound of molecular weight 482 corresponds to peak 6.

The preferred assay system for analyzing the human immunodeficiency virus (HIV) replication activity in associated in accordance to the present invention is the Reverse Transcriptase system. According to studies in the relevant field, the viral activity can be determined by way of a Reverse Transcriptase Assay. Inhibition of reverse transcriptase is thus indicative of anti-viral and more specifically anti-HIV activity when HIV reverse trancriptase is used in the assay.

Commercial Reverse Transcriptase Assay Kits were Used to Confirm the Anti-HIV Properties of the Fractions.
Calometric Roche™ Reverse Transcriptase Assay This is a colorimetric enzyme immunoassay for the quantitative determination of retroviral reverse transcriptase activity by incorporation of dioxigenein- and biotin-labeled dUTP into DNA.

The Calometric Roche™ Reverse Transcriptase Assay, takes advantage of the ability of reverse transcriptase to synthesize DNA, starting from the template/primer hybrid poly (A)×oligo (dT)15. Digoxigenin- and biotin-labeled nucleotides in an optimized ratio are incorporated into one and the same DNA molecule, which is freshly synthesized by the RT. The detection and quantification of synthesized DNA as a parameter for RT activity follows a sandwich ELISA protocol: Biotin-labeled DNA binds to the surface of microtiter plate (MTP) modules that have been precoated with streptavidin. In the next step, an antibody to digoxigenin, conjugated to peroxidase (anti-DIG-POD), binds to the digoxigenin-labeled DNA. In the final step, the peroxidase substrate ABTS is added. The peroxidase enzyme catalyzes the cleavage of the substrate, producing a colored reaction product. The absorbance of the samples can be determined using a microtiter plate (ELISA) reader and is directly correlated to the level of RT activity in the sample.

Figure 2:
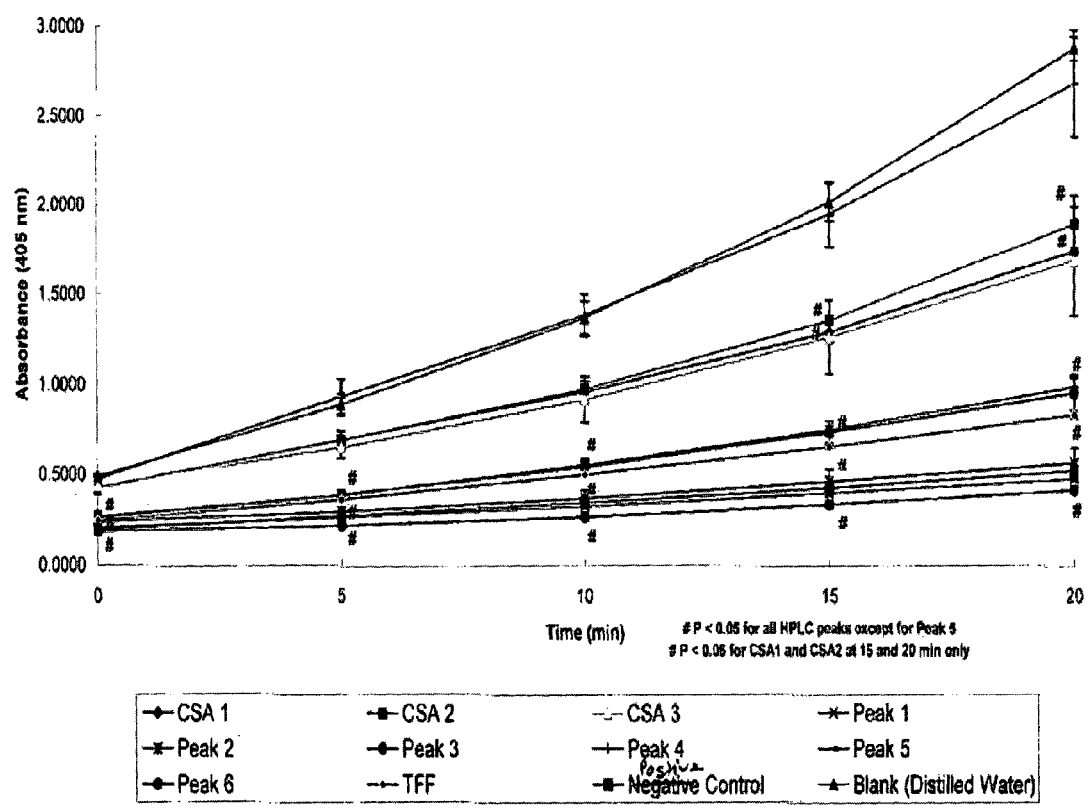
FIG. 2 shows the results obtained based on Reverse Transcriptase Assay with respect to the compound in accordance with a preferred embodiment of the claimed invention.

Accordingly, the fraction was prepared at various concentrations in both the dried and aqueous form. The four fractions from flash chromatography were also prepared with varying concentrations. It is observed that peak 6 exhibited significant and the highest inhibitory action, as seen in FIG. 2.

The novel compound of the claimed invention may be prepared for use in a pharmaceutically effective or nutraceutically effective amount, solely on its own or in combination with other agents or compounds deemed appropriate by a person skilled in the art. Further, compositions may be prepared in a manner, and in a form/amount as is conveniently practised.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The invention claimed is:

1. A method for scavenging a free radical in a subject in need thereof comprising administering an effective amount of a pharmaceutical or nutraceutical composition to said subject,
    wherein the composition comprises a bioactive compound having a molecular weight of 482, and wherein said bioactive compound is obtained by a method comprising:
    extracting oil palm based materials obtained from a palm oil milling effluent or palm vegetation liquor to obtain an extract;
    eluting said extract with methanol or ethanol;
    concentrating the extract in a rotary evaporator to obtain a concentrated extract; and
    isolating and purifying the bioactive compound from said concentrated extract.

2. A method for inhibiting a HIV reverse transcriptase in a subject in need thereof comprising administering an effective amount of a pharmaceutical or nutraceutical composition to said subject,
    wherein the composition comprises a bioactive compound having a molecular weight of 482, and wherein said bioactive compound is obtained by a method comprising:
    extracting oil palm based materials obtained from a palm oil milling effluent or palm vegetation liquor to obtain an extract;
    eluting said extract with methanol or ethanol;
    concentrating the extract in a rotary evaporator to obtain a concentrated extract; and
    isolating and purifying the bioactive compound from said concentrated extract.

* * * * *